(12) United States Patent
van der Weide et al.

(10) Patent No.: US 7,183,055 B2
(45) Date of Patent: Feb. 27, 2007

(54) DIRECT RADIO-FREQUENCY DETECTION OF NUCLEOTIDE HYBRIDIZATION AT MICROELECTRODES

(75) Inventors: Daniel W. van der Weide, Madison, WI (US); Robert J. Hamers, Madison, WI (US); John R. Peck, Madison, WI (US); Wei Cai, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 303 days.

(21) Appl. No.: 10/694,028

(22) Filed: Oct. 27, 2003

(65) Prior Publication Data

US 2004/0086929 A1     May 6, 2004

Related U.S. Application Data

(60) Provisional application No. 60/422,907, filed on Nov. 1, 2002.

(51) Int. Cl.
*C12Q 1/68* (2006.01)
*C12M 1/00* (2006.01)
*C07H 21/02* (2006.01)
*C07H 21/04* (2006.01)

(52) U.S. Cl. .......... 435/6; 435/283.1; 536/23.1; 536/24.3

(58) Field of Classification Search .......... 204/193, 204/403.01; 435/6, 283.1, 287.2; 536/23.1, 536/24.3
See application file for complete search history.

(56) References Cited

U.S. PATENT DOCUMENTS 4,713,347 A * 12/1987 Mitchell et al. .......... 436/501
6,060,023 A * 5/2000 Maracas .................. 422/68.1
6,090,933 A * 7/2000 Kayyem et al. .......... 536/25.3
6,756,223 B2 * 6/2004 Roberts et al. .......... 435/287.2

OTHER PUBLICATIONS

Souteyrand, et al., "Direct Detection of the Hybridization of Synthetic Homo-Oligomer DNA Sequences by Field Effect," *J Phys Chem B* (101) pp. 2980-2985, 1997.
Berggren, et al, "A Feasibility Study of a Capacitive Biosensor for Direct Detection of DNA Hybridization," *Electroanalysis* (11) 3: pp. 156-160, 1999.
Souteyrand, et al., "Comparison Between Electrochemical and Optoelectrochemical Impedance Measurements for Detection of DNA Hybridization," *J Appl. Biochem Biotech* (89) : pp. 195-207, 2000.
Berney, et al., "A DNA Diagnostic Biosensor: Development, Characterisation and Performance," *Sensors and Actuators B 68*, pp. 100-108, 2000.
W. Cai, et al., Abstract for AVS 49th International Symposium, available on the worldwide web at www.avssymposium.org at least as early as Oct. 26, 2002.

* cited by examiner

*Primary Examiner*—Ethan Whisenant
(74) *Attorney, Agent, or Firm*—Foley & Lardner LLP

(57) ABSTRACT

Radio-frequency (RF) excitation is used for direct detection of hybridization events at microelectrodes with surface-attached DNA oligomers. A homodyne reflectometer operates on a high frequency carrier to detect the presence of a low-frequency modulation signal. Without non-linearities in an interface, the modulation signal is not impressed upon the carrier signal. As such, the reflectometer can sensitively measure changes in dielectric properties without interference from other sources of capacitance/resistance unrelated to the reaction at the surface.

16 Claims, 4 Drawing Sheets

SEQUENCE LISTING

<160> NUMBER OF SEQ ID NOS: 3

<210> SEQ ID NO 1
<211> LENGTH: 16
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 1
aacgatcgag ctgcaa                                                     16

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aacgatgcag gagcaa                                                     16

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ttgcagctcg atcgtt                                                     16
```

DIRECT RADIO-FREQUENCY DETECTION OF NUCLEOTIDE HYBRIDIZATION AT MICROELECTRODES

CROSS-REFERENCE TO RELATED APPLICATIONS

The present application claims priority to U.S. Provisional App. No. 60/422,907 filed on Nov. 1, 2002, which is incorporated herein by reference.

REFERENCE TO GOVERNMENT RIGHTS

This invention was made with United States government support awarded by the following agencies: ONR N00014-01-1-0654. The United States government has certain rights in this invention.

FIELD OF THE INVENTION

This invention pertains generally to the field of biosensors and particularly to sensors for the detection of hybridization events.

BACKGROUND OF THE INVENTION

The use of biologically modified surfaces as active sensing regions for detection, identification, and sequencing of biological molecules is being intensively studied. In most sensors, selectivity is achieved by binding a known probe to the surface. The binding of the target molecules in the sample to the probe is detected by the generation of some physical or chemical signal. Several different read-out techniques, including optical, mass sensitive and electrochemical techniques are in present use. Many of these existing techniques require the use of fluorescent tags or other labels. The use of such fluorescent tags or other labels increases the complexity and cost of the detection techniques. Thus, there is significant interest in the development of sensor technologies that are label free. The use of electrical signals to sense biological binding events is particularly attractive because electrical measurements can be readily integrated with microprocessing and communication systems, potentially providing completely integrated sensing systems. Previous electrical detection systems have primarily focused on capacitance and/or electrochemical responses as the primary means of signal detection. It is desirable to miniaturize such detection systems to reduce costs and allow parallel processing, but as the physical size of the sensing region becomes smaller, employing current detection schemes which depend on measurements of changes in current can be difficult and unreliable, limiting the response time and sensitivity.

SUMMARY OF THE INVENTION

In accordance with the invention, highly sensitive detection of hybridization events may be localized to a very small sensing region. Hybridized nucleotides in a cell sample alter an electrical double-layer having a nonlinear response to applied high frequency electromagnetic fields, resulting in increased mixing and modulation of a high frequency signal by a low frequency signal applied to the sample. The presence of modulation in the high frequency signal indicates that hybridization has occurred in the localized area to which the signal is applied. Detection of hybridization in this manner provides a nearly zero-background technique for sensing changes in the electrical double layer at microelectrode surfaces because of the absence of non-linearity in the bulk of the sample fluid in the cell.

Further objects, features and advantages of the invention will be apparent from the following detailed description when taken in conjunction with the accompanying drawings.

DETAILED DESCRIPTION OF THE EXEMPLARY EMBODIMENTS

Figure 1:
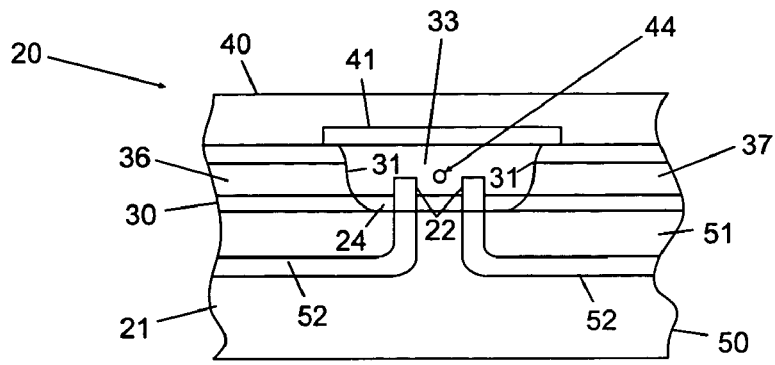
FIG. 1 is a simplified cross-sectional view of a flow cell for holding a sample for use in an exemplary embodiment.
Figure 2:
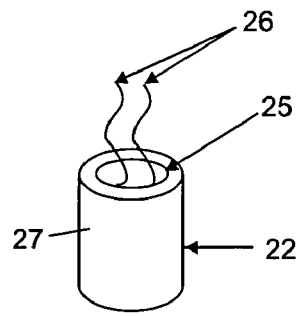
FIG. 2 is a simplified perspective view of a working electrode of the flow cell of FIG. 1, illustrating the immobilization of nucleotides on an exposed surface of the working electrode.

With reference to the drawings, an exemplary flow cell structure that may be utilized in a radio frequency detection apparatus is shown generally at 20 in FIG. 1 in cross-section. The flow cell 20 includes a base 21 with working electrodes 22 (two shown), mounted therein and extending above a top surface 24 of the base into a region in which a sample fluid may be held. As best illustrated in FIG. 2, the exposed portions of the working electrodes 22 include an exposed terminal surface 25 (e.g., having a gold coating, as discussed below) on which the nucleotide (illustratively shown at 26) may be immobilized. The central core conductor (e.g., of gold) which terminates on the surface 25 is preferably insulated from the surrounding sample by a layer of insulation 27 (e.g., polyimide)

The flow cell 20 further includes an intermediate layer 30 which includes interior walls 31 defining the peripheral walls of a flow cell chamber 33, an inlet channel 36 extending from an inlet end to communication with the flow cell cavity 33 by which sample fluid may be provided to the cell, and an outlet channel 37 extending from communication with the cavity 33 to an outlet end by which sample fluid may be discharged from the cell. The multilayer flow cell structure 20 is completed by a top panel 40 in which is embedded a counter-electrode 41 which closes the top of the flow cell chamber 33. A reference electrode 44 is embedded in the intermediate panel 30 in position to be in contact with the sample fluid within the flow cell chamber 33.

Figure 3:
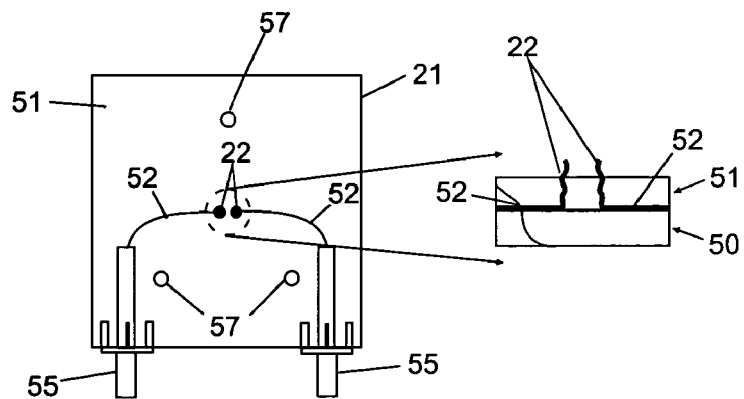
FIG. 3 is a top view of a base for the flow cell of FIG. 1.

As illustrated in FIGS. 1 and 3, the base 21 may be formed with a rigid bottom layer 50 (such as a circuit board) on which other electrical components (not shown) may be mounted, and with an insulating layer 51 in which the conducting wires 52 extending to the working electrodes 22 may be embedded. For example, the insulating layer 51 may be formed of polydimethylsiloxane (PDMS). The conducting wires 52 extend through the insulating layer 51 to connectors 55 by which connections may be made to external electronic components. Openings 57 may be formed in the base 21 by which the base 21 may be firmly connected by bolts (not shown) to the intermediate layer 30 and the top layer 40 of the flow cell structure.

Figure 4:
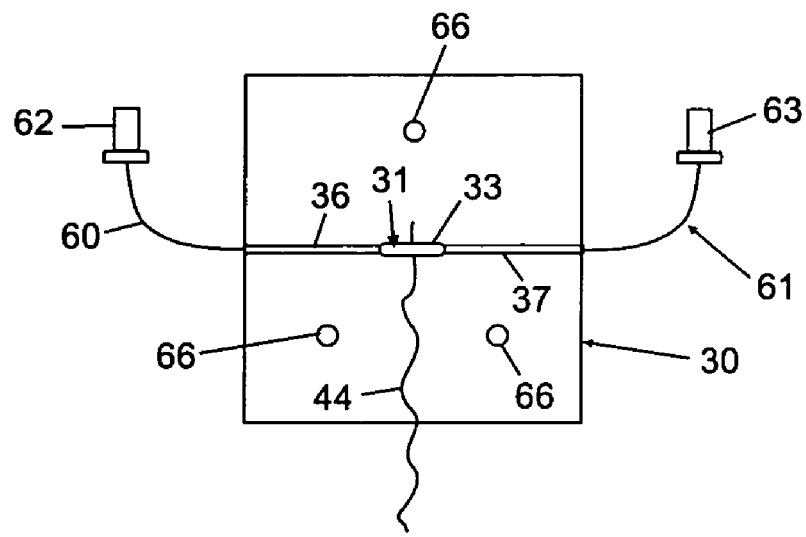
FIG. 4 is a plan view of an intermediate flow cell layer including a reference electrode and input and output channels for the flow cell.

As illustrated in the top view in FIG. 4 of the intermediate layer 30, the inlet channel 36 is connected to tubing 60 and the outlet channel 37 is connected to tubing 61 (e.g., Teflon PTFE tubing), with couplings 62 and 63 at the ends of the tubes 60 and 61, respectively, to allow connection to a source of biochemicals and to disposal. The wire 44 forming the reference electrode may be embedded in the insulating material of the layer 30. The reference electrode 44 may be formed of, e.g., Ag/AgCl, and the material of the layer 30 may be formed of an insulating polymer such as PDMS. Openings 66 are formed in the layer 30 through which bolts may be passed to secure the intermediate layer to the base 21 and the top layer 40.

Figure 5:
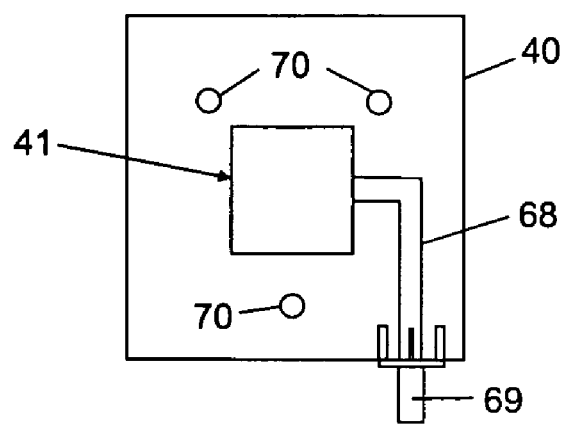
FIG. 5 is a plan view of the top structure of the flow cell of FIG. 1 including an embedded counter-electrode.

As shown in FIG. 5, the top layer 40 of the flow cell (formed of an insulating material such as PDMS) has the counter-electrode 41 embedded therein with a conductor 68 extending from the counter-electrode 41 to a connector 69 by which an electrical connection can be made from external electronics to the counter-electrode 41. The counter-electrode 41 is preferably formed of a non-reactive conductive material such as glassy carbon. Openings 70 are formed in the layer 40 to again allow bolts to be passed therethrough to enable the top layer 40 to be bolted to the intermediate layer 30 and to the base 21.

Figure 6:
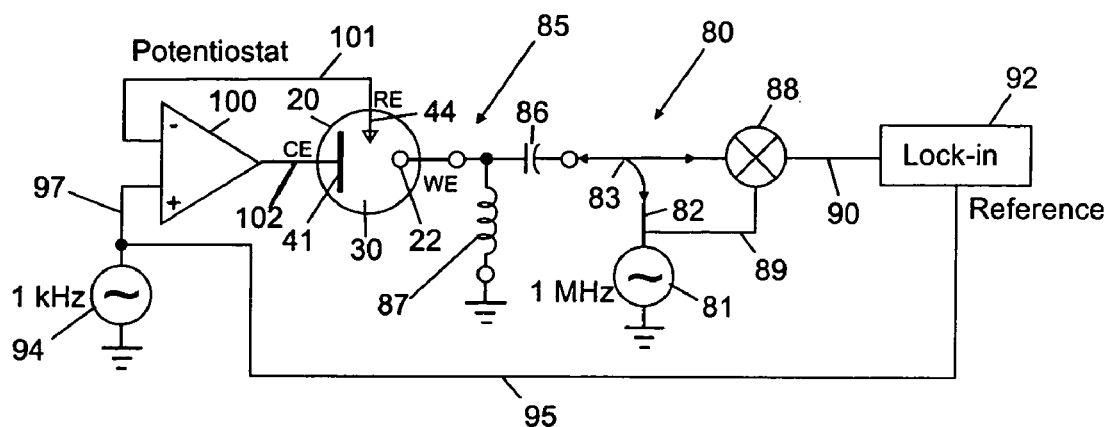
FIG. 6 is a schematic diagram of the detection apparatus according to an exemplary embodiment.

A schematic diagram of the detection apparatus of the invention including the flow cell 20 is shown generally at 80 in FIG. 6. The detection apparatus 80 includes a high frequency signal generator 81 which supplies a high frequency sinusoidal signal (e.g., at 1 MHz) on an output line 82 to a directional coupler 83. The output of the directional coupler is transmitted to the working electrode 22 via a high pass filter bias Tee network 85, composed of a capacitance 86 and inductance 87, to couple the high frequency signal to a working electrode 22 within the flow cell 20. The reflected signal from the working electrode 22 is passed back through the bias Tee 85 and the directional coupler 83 to a mixer 88. The mixer 88 also receives on a line 89 the high frequency signal from the high frequency signal generator 81. The mixer 88 mixes the received signal passed back through the directional coupler 83 and the high frequency signal from the signal generator 81 to provide an output signal on a line 90 to a detector 92 which may be formed as a lock-in amplifier.

The detector 92 also receives a low frequency signal (e.g., at 1 kHz) from a low frequency signal generator 94 on a line 95. The low frequency signal generator 94 also provides the low frequency signal on a line 97 to the positive input of a potentiostat 100. The voltage on the reference electrode 44 is conducted back by a line 101 to the negative input of the potentiostat 100, and the output of the potentiostat 100 on a line 102 is provided to the counter-electrode 41. The voltage thus provided to the counter-electrode 41 is a signal at a frequency much lower than that of the primary excitation signal from the signal generator 81, and preferably non-harmonically related to it, with the voltage applied to the counter-electrode 41 referenced to the reference electrode 44.

Hybridization of nucleotides bound to the exposed surface 25 of the working electrode 22 changes the non-linear characteristics inherent in the electrode/solution interface, thereby changing the efficiency of frequency mixing at the interface. The reflected signal from the working electrode 22 is passed back through the bias Tee 85 and the directional coupler 83 to the mixer 88. This reflected signal from the working electrode 22 constitutes a signal at the high excitation frequency from the signal generator 81 modulated by the low frequency signal from the low frequency signal generator 94. The mixer 88 mixes (homodynes) the modulated signal with the carrier frequency signal from the source 81 to provide an output signal on the line 90 at the low excitation frequency (e.g., 1 kHz). This signal is detected by the detector 92 by utilizing the reference signal (e.g., at 1 kHz) from the low frequency signal generator 94 to lock into the low frequency signal on the line 90, providing an indication of the amplitude of modulation, thereby indicating whether hybridization has taken place. As shown in FIG. 1, two (or more) working electrodes 22 may be utilized. A bias Tee 85 may be connected to each of the electrodes 22 (or to each one of many working electrodes) and the bias Tees may be selectively connected via a switch (not shown in FIG. 6) to the directional coupler 83 to allow multiple electrodes to be analyzed.

The following examples illustrate the use of the apparatus 80 to detect hybridization events. In these examples, the apparatus 80 utilizes chemically- or biologically-modified gold wires that act as the working electrodes 22, a Ag/AgCl reference electrode 44, and a glassy carbon counter electrode 41. The electrodes 22 are embedded in polydimethylsiloxane (PDMS), with a cell chamber 33 volume of approximately 20 µl. The gold wires 22 are coated with polyimide 27 (e.g., a KAPTON polyimide) except for the circular cross-sectional area 25 at the very end of the wires. The layers 30 and 40 and the copper-clad circuit boards 22 are bolted together to close the fluid cell and position the electrodes.

Before insertion into the PDMS support, the Au working electrodes 22 are fixed in a hollow alumina rod with crystal bond for hand polishing. An example bond is a Type 509 bond available from Electron Microscopy Sciences. The rod and wire ends are polished starting with 320 grit silicon carbide paper and with progressively finer grits down to 1 and 0.3 µm slurries on polishing cloths. The wires are released from the crystal bond with acetone, followed by rinsing with methanol and ultrapure water.

The released wires are exposed to ozone generated by a low pressure mercury lamp for 5 minutes and rinsed again with ultrapure water. After a brief rinse with 200-proof ethanol, the wire ends are blown dry under a stream of nitrogen gas. These wire ends are modified with alkanethiols by soaking in $N_2$-purged 1 mM ethanol solution of the alkanethiol in sealed vials for at least 40 hrs.

Prior to impedance measurements, the SAM (self assembled monolayer)-coated wire ends are thoroughly rinsed with absolute ethanol and ultrapure water. Impedance measurements of these SAM-coated surfaces are obtained with an electrochemical interface combined with an impedance analyzer and a three-electrode cell, with the modified Au surfaces as working electrodes, a Pt wire counter electrode, and a Ag/AgCl wire reference electrode. The impedance spectra are fit to a series resistor and constant-phase-element (CPE) using a Zplot/Zview software package.

A phase angle exceeding 88° at 1 kHz and a CPE exponent exceeding 0.88 indicates a usable working electrode for DNA attachment. Usable electrodes are inserted into the flow cell 20 and cleaned as before with ozone, water, and ethanol. In order to attach DNA on to the wire end, 11-mercaptoundecylamine (MUAM) is used to form SAMs that bear primary amine groups at the end. The primary amine groups react with a heterobifunctional cross-linker sulfosuccinimidyl-4-(N-maleimidomethyl)cyclohexane-1-carboxylate (SSMCC) while soaking in 1.5 mM SSMCC solution for 20 minutes. After thoroughly rinsing with DI (deionized) water, these surfaces are incubated in thiol-modified DNA at room temperature overnight.

As illustrated in FIG. 6, a standard type of potentiostat structure 100 is used to apply a 1 kHz sinusoidal modulation to the glassy carbon counter-electrode 41. The radio-frequency (typically 1 MHz) carrier is also applied through the directional coupler 83 (e.g., ZFDC-15-6) to the functionalized gold working electrode 22. With capacitive and/or resistive nonlinearity at the double-layer, the electrical signal reflected from the working electrode contains signal components at 1 kHz, 1 MHz, and the sum and difference frequencies (upper and lower sidebands) generated by mixing in the electrical double-layer region.

The modulated signal reflected from the double-layer is high-pass filtered by the bias Tee 85 (200 nF capacitance 1 mH inductance) to reject any remnant of the original 1 kHz signal and then applied to a conventional frequency mixer 88 (e.g., ZAD-8) whose local oscillator is the 1 MHz carrier from the signal generator 81. This separates (coherently demodulates) the 1001 and 999 kHz sidebands from the 1 MHz carrier and the sidebands are detected using a lock-in amplifier 92 (e.g., SR 830) whose reference is the 1 kHz modulation signal from the low frequency signal generator 94. If there exists a capacitance at the electrode whose response to an applied electric field is not linear, this response will have second-and higher-order terms in its polynomial expansion. The second-order term squares the sum of the carrier signal (1 MHz) and modulation signal (1 kHz), multiplying the signals to give rise to the sidebands that are detected. In the absence of non-linearity, no such signal multiplication takes place. Thus, the system exhibits very low background.

To test the response of the apparatus 80, experiments were performed on gold surfaces that were chemically modified with 11 Mercaptoundecanoic acid (MUA) and 11-Amino-1-undecanethiol (MUAM) to produce surfaces terminated with amine or carboxylic acid groups, and changes in response were measured as a function of solution pH. Similar electrochemical titrations have been performed using capacitance measurements, with the measured pKa's for surface acids and bases differing significantly from their bulk solution values due to surface roughness, electrostatic interactions, hydrogen bonding, local surface dielectric constants, and double-layer effects.

Figure 7:
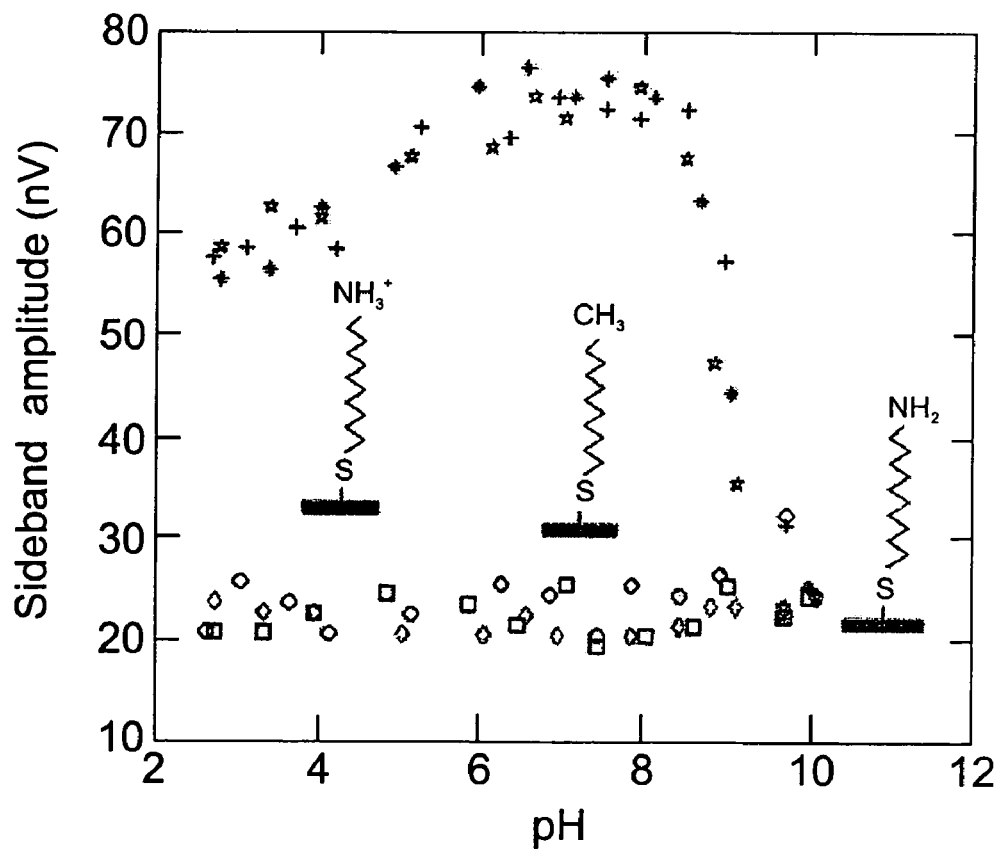
FIG. 7 are graphs of typical data from a pH sweep using amine-and methyl-terminated working electrode surfaces.

FIG. 7 shows mixing data obtained simultaneously from two different gold microelectrodes 22 in the same cell. One microelectrode 22 was chemically modified with undecanethiol, and the other microelectrode was modified with MUA or MUAM. Thus, the first electrode is terminated with a methyl group, while the second presents a carboxylic acid or amine to the solution. The solution consisted of 0.1 M KCl, with the pH set by adding 0.1 M HCl or KOH. FIG. 7 shows that the amine-terminated surface produces a large change in the mixing signal as long as the solution pH is varied, while the methyl-terminated surface response is completely independent of pH. To demonstrate the reversibility and stability, FIG. 7 also shows two successive sweeps, which reveal nearly identical traces. Thus, the data show non-linear frequency mixing can be used to probe the changes in dielectric response at the gold-solution interface.

To test the application of the detection method to the important problem of biological detection, experiments were performed in which gold microelectrodes 22 embedded in PDMS (with the ends exposed) were chemically modified with two different sequences of DNA. The first electrode was modified with DNA having the sequence 5'-HS—$C_6H_{12}$-$T_{15}$AACGATCGAGCTGCAA3' (SEQ ID No: 1), while the second was modified with the sequence 5'-HS—$C_6H_{12}$-$T_{15}$AACGATGCAGGAGCAA3' (SEQ ID No: 2). These oligonucleotides, which have a 4-base difference between them, were bonded to the gold surface using chemistry described in Brockman, et al., "A multi-step chemical modification procedure to create DNA arrays on gold surfaces for the study of protein—DNA interactions with surface plasma on resonance imaging," J. of Am. Chem. Soc., Vol. 121, No. 35, 1999, pp. 8044 et seq.

The cell was filled with SSPE buffer, 2×, consisting of 300 mM NaCl, 20 mM sodium phosphate and 2 mM EDTA, and the response was measured. The cell was then flushed and filled with 5 μM 5'TTGCAGCTCGATCGTT3' (SEQ ID No: 3), which represents a perfect match with SEQ ID No: 1 and a four-base mismatch with SEQ ID No: 2. After allowing 20 minutes for hybridization to occur, the solution was replaced with the buffer, and the response was again measured.

Figure 8:
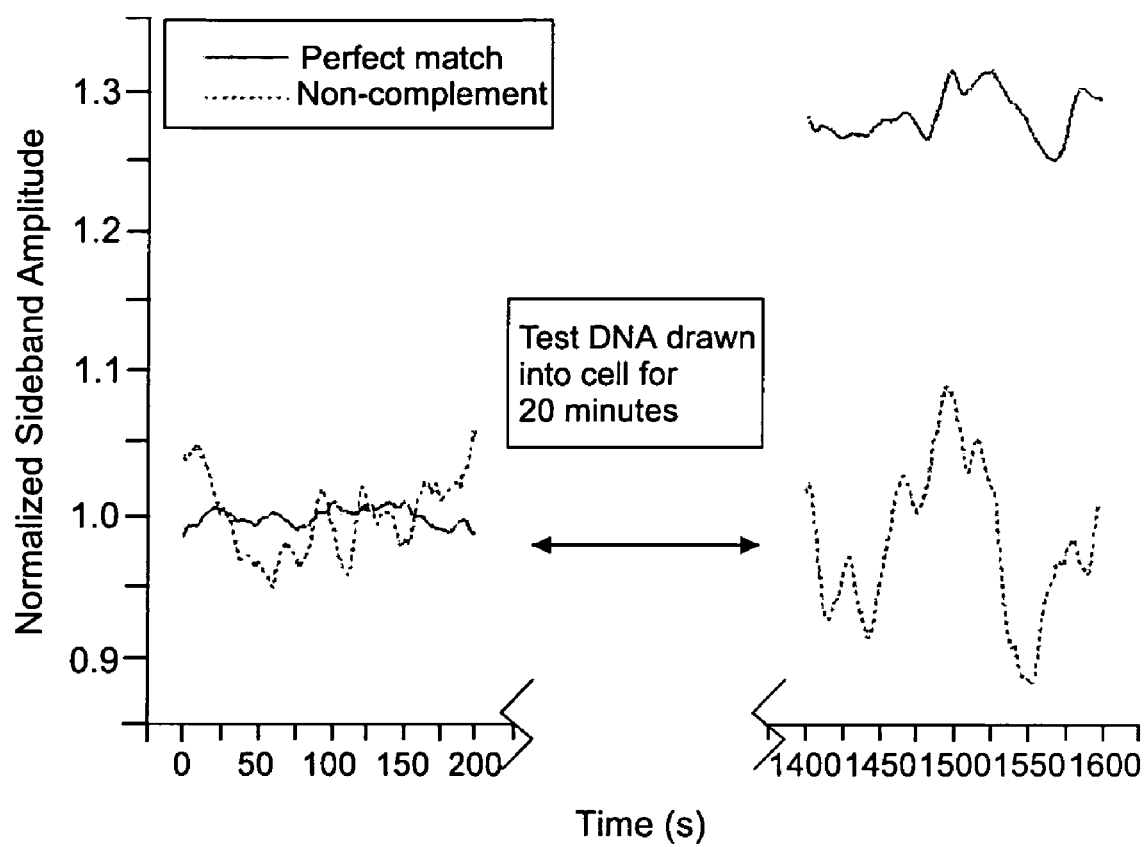
FIG. 8 are graphs showing typical data taken before and after DNA hybridization utilizing the detection apparatus of an exemplary embodiment.

FIG. 8 shows that the gold wire functionalized with sequence $s_1$ exhibits a pronounced increase in the sideband amplitude, while the wire functionalized with $S_2$ showing almost no change. Thus, this method is able to detect the changes in the dielectric properties of the electrical double-layer that accompany DNA hybridization. This reaction has been independently verified using fluorescently labeled DNA on gold surfaces.

In general, it is expected that the dielectric properties such as conductivity and capacitance of the solid-liquid interface will change in response to biological binding events. The apparatus and methods described have the particular advantage of an ability to isolate the active sensing region from the background using the non-linear response of the electrical double-layer. The Gouy-Chapman theory has been used to describe the non-linear properties of the electrical double-layer at electrolyte-electrode interfaces. See, e.g., D. Mohilner, "The electrical double layer, part 1: Elements of double layer theory," in Electroanalytical Chemistry, A. J. Bard, editor, Manual Dekker, Inc., New York, 1966, p. 241. Any process that modifies the chemical or physical structure of the solid-liquid interface can, therefore, generate a signal that can be detected using this method.

It is understood that the invention is not confined to the particular embodiments set forth herein as illustrative, but embraces all such forms thereof as come within the scope of the following claims.

What is claimed is:

1. Apparatus for detection of nucleotide hybridization comprising:
   (a) cell walls defining a cell for holding a sample fluid;
   (b) at least one working electrode mounted with an electrode surface in the cell, the electrode surface being configured for attachment to nucleotides;
   (c) a counter-electrode mounted in the cell at a position spaced from the working electrode and positioned to be in contact with sample fluid in the cell;
   (d) a first frequency signal generator connected via a directional coupler to the working electrode to apply a signal at a first frequency thereto;
   (e) a second frequency signal generator connected to the counter-electrode to provide a signal to the counter-electrode at a frequency lower than the first frequency signal applied to the working electrode;
   (f) a mixer connected via the directional coupler to the working electrode, the mixer adapted to receive a signal reflected from the working electrode and connected to the first frequency signal generator, the mixer providing an output signal that is the mix of the first frequency signal from the first frequency signal generator and the signal received through the directional coupler from the working electrode; and
   (g) a signal detector adapted to receive the output signal from the mixer and to detect modulation of the first frequency signal by the second frequency signal thereby indicating hybridization.

2. The apparatus of claim 1 further including a reference electrode mounted in the cell spaced from the working electrode and the counter-electrode and positioned to be in contact with sample fluid in the cell, the second frequency signal generator connected to the counter-electrode through the positive input of a potentiostat having a negative input which is connected to the reference electrode.

3. The apparatus of claim 1 wherein the signal detector includes a lock-in amplifier receiving the output signal from the mixer and the signal from the second frequency signal generator.

4. The apparatus of claim 1 wherein the first frequency from the first frequency signal generator is about 1 MHz and the second frequency signal from the second frequency signal generator is at about 1 kHz.

5. The apparatus of claim 1 further including a bias Tee connected between the directional coupler and the working electrode.

6. The apparatus of claim 1 wherein there are a plurality of working electrodes mounted in the cell.

7. The apparatus of claim 1 including an inlet channel extending to communication with the cell by which sample fluid may be provided to the cell, and an outlet channel extending from communication with the cell by which sample fluid may be discharged from the cell.

8. The apparatus of claim 7 wherein the sample cell is formed in a multilayer structure having a base in which the working electrode is mounted and in which a conductor extending to the working electrode is embedded, an intermediate layer defining therein the inlet and outlet channels and peripheral walls of the cell, and a top layer having the counter-electrode embedded therein.

9. The apparatus of claim 1 further comprising a self-assembled monolayer formed on the electrode surface of the working electrode.

10. A system configured to detect nucleotide hybridization, the system comprising:

(a) a fluid sample cell having at least one working electrode mounted therein and a counter electrode mounted therein at a distance from the at least one working electrode;
(b) a first signal generator coupled to the least one working electrode;
(c) a second signal generator coupled to the counter electrode; and
(d) a mixer adapted to receive a first signal reflected from the first signal generator, to receive a second signal from the first signal generator, and to mix the received first signal and the received second signal;
(e) a detector adapted to receive the signal mix and to detect modulation in the signal mix, thereby indicating hybridization in a sample in the fluid sample cell.

11. The system of claim 10, wherein the first signal generator provides a signal of at least 1 MHz.

12. The system of claim 10, wherein the at least one working electrode comprises an electrode surface covered in gold.

13. The system of claim 12, wherein the electrode surface has an area of at least 0.01 $mm^2$.

14. The system of claim 10, wherein the at least one working electrode comprises an electrode surface covered with a self-assembled monolayer.

15. The system of claim 10, wherein the first signal generator is coupled to the at least one working electrode by a directional coupler.

16. The system of claim 15, further comprising a bias Tee connected between the directional coupler and the at least one working electrode.

* * * * *